United States Patent
Song et al.

(10) Patent No.: US 7,806,376 B2
(45) Date of Patent: Oct. 5, 2010

(54) MEDICAL INSTRUMENT

(75) Inventors: Mi Ran Song, Seoul (KR); Jae-Gyoung Kim, Seoul (KR); Young Seuk Song, Seoul (KR); Sun ki Lee, Seoul (KR); Soo-Hwan Shin, Seoul (KR)

(73) Assignee: Medison Co., Ltd., Gangwon-do (KR)

( * ) Notice: Subject to any disclaimer, the term of this patent is extended or adjusted under 35 U.S.C. 154(b) by 0 days.

(21) Appl. No.: 12/404,529

(22) Filed: Mar. 16, 2009

(65) Prior Publication Data

US 2010/0001149 A1 Jan. 7, 2010

(30) Foreign Application Priority Data

Jul. 3, 2008 (KR) ...................... 10-2008-0064563

(51) Int. Cl.
A47B 37/00 (2006.01)
F16M 11/02 (2006.01)

(52) U.S. Cl. ............... 248/177.1; 248/129; 248/346.03; 248/500; 108/50.01

(58) Field of Classification Search .............. 248/177.1, 248/680, 500, 506, 510, 346.03, 346.06, 248/346.07, 129, 346.04; 108/50.01, 147
See application file for complete search history.

(56) References Cited

U.S. PATENT DOCUMENTS

| 2,781,803 | A | * | 2/1957 | Nelson | 269/91 |
| 3,408,032 | A | * | 10/1968 | Francis | 248/450 |
| 4,852,836 | A | * | 8/1989 | Kawazoe | 248/168 |
| 5,088,420 | A | * | 2/1992 | Russell | 108/106 |
| 5,623,869 | A | * | 4/1997 | Moss et al. | 108/43 |
| 6,010,121 | A | * | 1/2000 | Lee | 269/94 |
| 6,093,039 | A | | 7/2000 | Lord | |
| 6,397,761 | B1 | * | 6/2002 | Moore | 108/50.01 |
| 6,491,268 | B1 | * | 12/2002 | Channer et al. | 248/176.1 |
| 6,585,212 | B2 | * | 7/2003 | Carnevali | 248/346.07 |
| 7,611,112 | B2 | * | 11/2009 | Lin | 248/274.1 |
| 2003/0231465 | A1 | | 12/2003 | Weng | |
| 2007/0131825 | A1 | * | 6/2007 | Skrodzki | 248/177.1 |
| 2007/0140475 | A1 | | 6/2007 | Kurtock et al. | |
| 2008/0078071 | A1 | | 4/2008 | Gong | |

* cited by examiner

*Primary Examiner*—Anita M King
(74) *Attorney, Agent, or Firm*—Jones Day (57) ABSTRACT

Disclosed is a medical instrument. The medical instrument includes a main body including at least one of an operation part and a display part, a cart including a desk on which the main body is positioned, a front detachable member disposed on the desk and adapted to attach and detach a front portion of the main body to/from the desk, and at least one rear detachable member disposed on the desk and adapted to attach and detach a rear portion of the main body to/from the desk and elastically support the rear portion of the main body.

4 Claims, 11 Drawing Sheets

MEDICAL INSTRUMENT

CROSS-REFERENCE TO RELATED APPLICATION

This application claims the benefit of Korean Patent Application No. 10-2008-0064563, filed on Jul. 3, 2008, in the Korean Intellectual Property Office, the disclosure of which is incorporated herein by reference.

BACKGROUND OF THE INVENTION

1. Field of the Invention

The present invention relates to a medical instrument, and particularly, to a medical instrument in which a main body of the medical instrument is easily mounted to or separated from a cart.

2. Description of Related Art

In general, medical instruments are devices used in conducting diagnosis or medical treatment of patients in hospitals or physicians' offices. These medical instruments may be useful to doctors, and allow the doctors to more easily and accurately conduct the diagnosis or medical treatment. With development in techniques, current medical instruments may show a trend of improving performance and convenience, getting smaller, and the like. In particular, when the medical instruments are getting smaller, a high space utilization of the hospital may be acquired due to a reduction in occupied areas of the medical instruments, and convenience of use of the medical instruments may increase due to being easily movable and operated.

However, a conventional medical instrument may have limitations in its convenience of use and miniaturization due to peripheral equipments even though the main body practically conducting medical treatments is relatively small in its size. As a representative example of the peripheral equipments, a structure used for supporting and moving the main body, controlling a height of the main body, and the like, or a storage for safekeeping accessories and consumption goods of the main body may be given. Accordingly, due to the limitation in miniaturization of the conventional medical instruments, a number of medical instruments may be used only in a separate consultation room, operating room, and the like. Also, disadvantageously, results of medical tests conducted using the medical instruments may be outputted as separate documents, photos, and the like, and provided to a doctor and a patient. Also, since the medical instruments may be difficult to be moved to the patient, high quality medical services are difficult to be acquired when medical services are provided at patients' residence.

A medical instrument of the present invention in which a main body practically conducting medical treatment may be easily mounted to and separated from a cart is disclosed.

A medical instrument of the present invention in which the main body separated from the medical instrument may be movable to various locations during ambulatory care to thereby conduct high quality medical services, and also to easily utilize data stored in the main body is disclosed.

SUMMARY OF THE INVENTION

An aspect of the present invention is to provide a medical instrument in which a main body practically conducting medical treatments may be easily mounted to and separated from a cart is disclosed.

Another aspect of the present invention is to provide a medical instrument in which the main body separated from the medical instrument may be movable to various locations during ambulatory care to thereby conduct high quality medical services, and also to easily utilize data stored in the main body is disclosed.

According to an aspect of the present invention, there is provided a medical instrument, including: a main body including at least one of an operation part and a display part; a cart including a desk on which the main body is positioned; a front detachable member disposed on the desk and adapted to attach and detach a front portion of the main body to/from the desk; and at least one rear detachable member disposed on the desk and adapted to attach and detach a rear portion of the main body to/from the desk and elastically support the rear portion of the main body.

In this instance, the front detachable member may include: at least one first front fixing part upwardly protruded from a front portion of the desk and adapted to support both side surfaces and front surface of the main body; and a second front fixing part movably disposed on the desk and adapted to enable a side of the second front fixing part to closely contact with an upper surface of the main body. Also, the side of the second front fixing part may be shaped to conform to the upper surface and front surface of the main body, so that the side of the second front fixing part is closely contacted with the upper surface and front surface of the main body at the same time.

In this instance, the at least one rear detachable member may include: a first rear fixing part disposed on another region of the desk different from a region where the main body is seated; a second rear fixing part disposed on an upper portion of the first rear fixing part in such a manner as to be elevated and rotated, and include a latching protrusion latched on an upper surface of the main body; and a third rear fixing part connected at a side with the first rear fixing part and connected at the other side with the second rear fixing part and adapted to elastically support the second rear fixing part.

Also, a through hole passing through upper and lower sides of the desk may be formed inside the first rear fixing part, and the third rear fixing part may include a rod connected at its top with the second rear fixing part and passing through the through hole, and an elastic member disposed between a lower portion of the rod and a lower portion of the first rear fixing part. Also, the first rear fixing part may include a first boss upwardly protruded and formed into a cylindrical shape, and the second rear fixing part downwardly protruded, formed into a cylindrical shape, and inserted in the first boss in such a manner as to be rotated and elevated.

According to another aspect of the present invention, the rear detachable member may include: a first rear fixing part disposed on a region of the desk where the main body is seated and inserted in and coupled with a latching groove formed on a lower portion of the main body when the main body is seated; a second rear fixing part having a side thereof connected with the first rear fixing part and, at the other side of the second rear fixing part, exposed outwardly from a rear portion of the desk; and a third rear fixing part disposed between any one of the first and second rear fixing parts and the desk and adapted to elastically support the first rear fixing part.

In this instance, a through hole may be formed on the desk to correspond to the latching groove of the main body, the first rear fixing part vertically passes through the through hole, and the through hole may be elongatedly formed in a moving direction of the first rear fixing part.

Also, the first rear fixing part may include a latching protrusion formed on an upper portion thereof and adapted to be inserted in and latched to the latching groove, and the third rear fixing part may include an elastic member disposed between a lower portion of the first rear fixing part and a lower portion of the desk. Also, a plurality of first rear fixing parts may be disposed on the desk, and the second rear fixing part may be disposed on a lower portion of the desk and connected at a side thereof with a lower portion of the plurality of first rear fixing parts.

According to another aspect of the present invention, there is provided a medical instrument, including: a main body including at least one of an operation part and a display part, and an insertion groove formed on a rear portion thereof; a cart including a desk on which the main body is positioned; a front detachable member disposed on the desk and adapted to attach and detach a front portion of the main body to/from the desk; and a rear detachable member slidingly disposed on a rear portion of the desk to enable the rear portion of the main body to be attached to and detached from the desk, and inserted in or separated from the insertion groove.

In this instance, the rear detachable member may include an insertion part inserted in the insertion groove, and a moving part disposed on a lower portion of the insertion part and slidingly disposed on the rear portion of the desk in a back and forth direction.

BRIEF DESCRIPTION OF THE DRAWINGS

The above and/or other aspects and advantages of the present invention will become apparent and more readily appreciated from the following detailed description, taken in conjunction with the accompanying drawings of which.

DETAILED DESCRIPTION OF EXEMPLARY EMBODIMENTS

Reference will now be made in detail to exemplary embodiments of the present invention, examples of which are illustrated in the accompanying drawings, wherein like reference numerals refer to the like elements throughout. The exemplary embodiments are described below in order to explain the present invention by referring to the figures.

Figure 1:
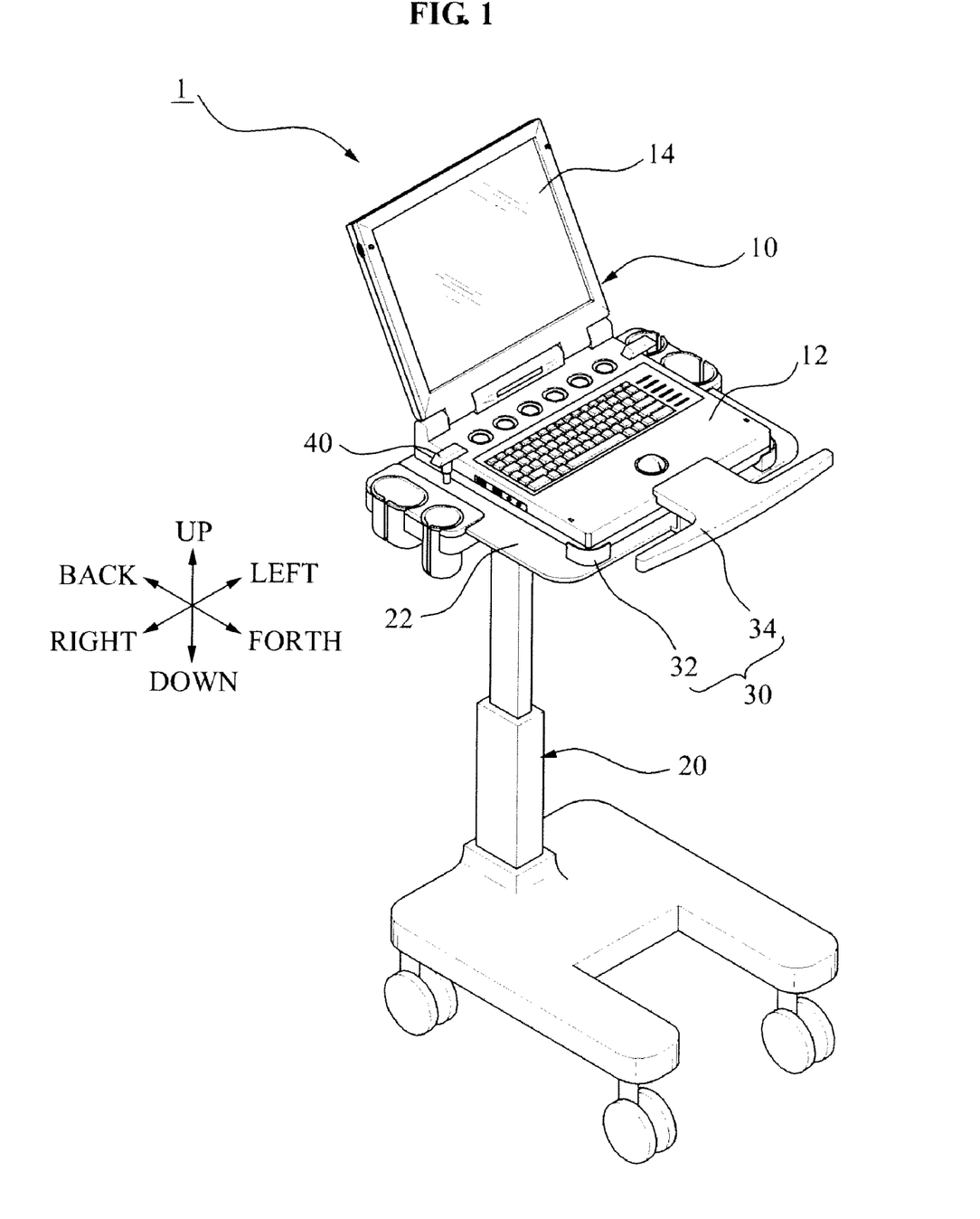
FIG. 1 is a perspective view showing a medical instrument according to an exemplary embodiment of the present invention.
Figure 2:
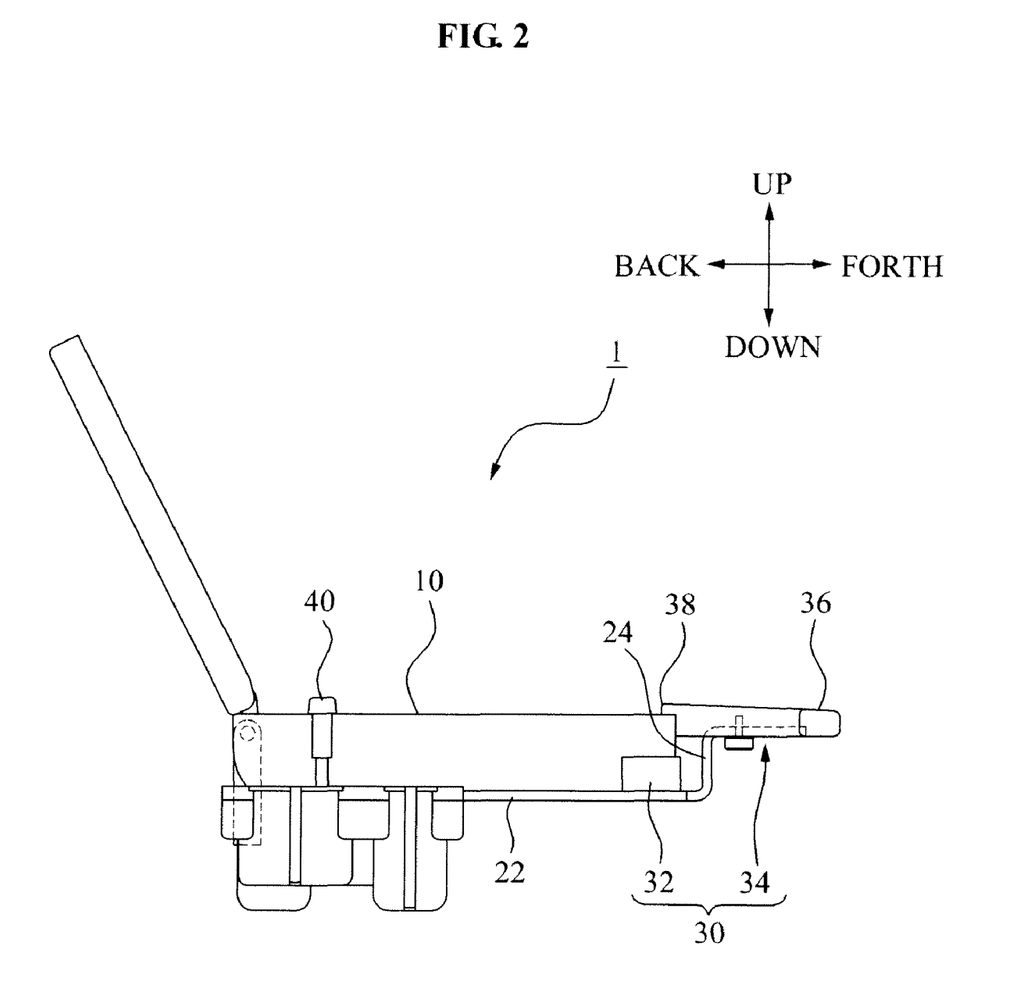
FIG. 2 is a side view showing a main body and desk of the medical instrument of FIG. 1.
Figure 3:
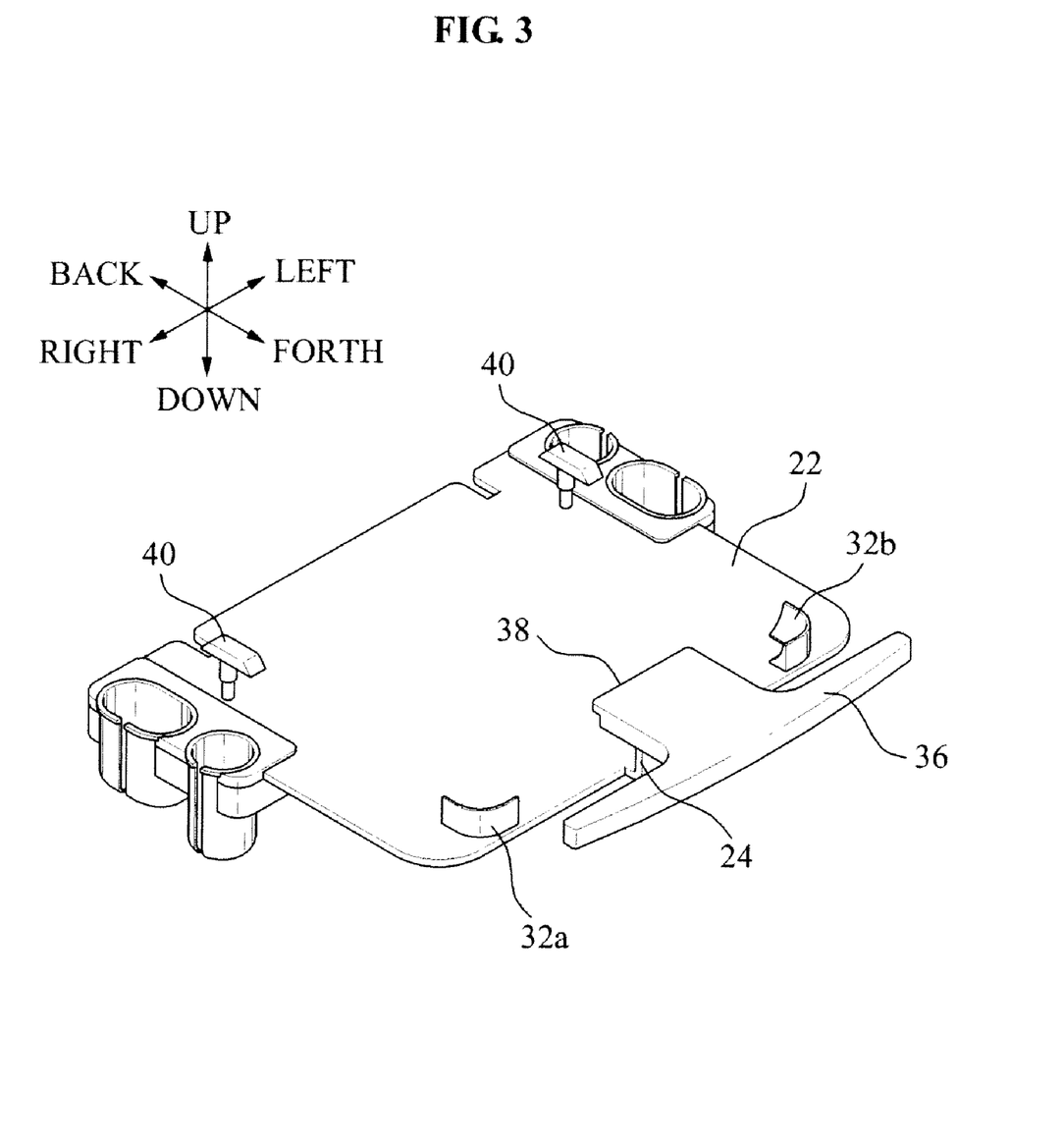
FIG. 3 is a perspective view showing the desk of the medical instrument of FIG. 1.
Figure 4:
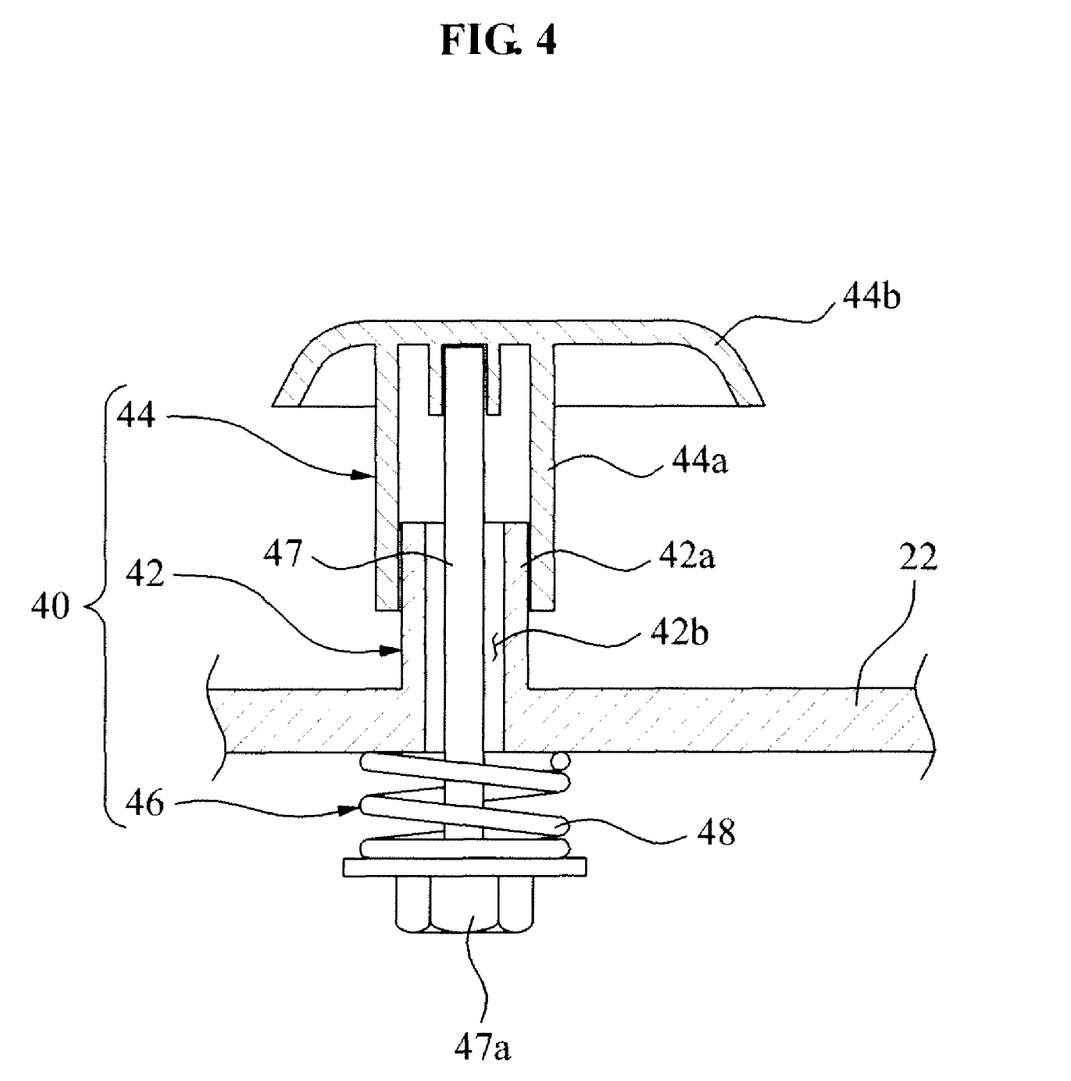
FIG. 4 is a cross-sectional view showing a rear detachable member of FIG. 1.
Figure 5:
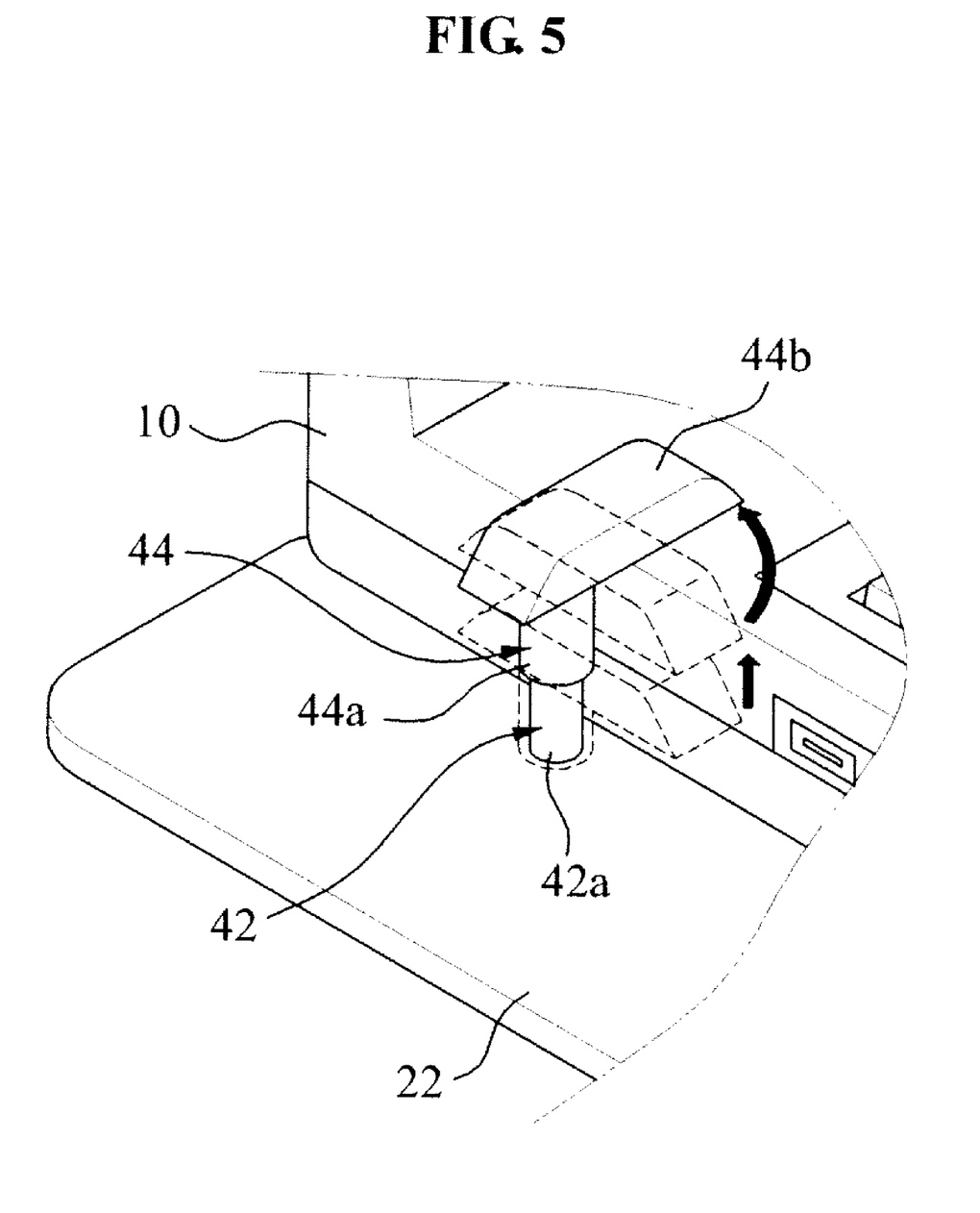
FIG. 5 is a perspective view showing an operation state of the rear detachable member of FIG. 1.

FIG. 1 is a perspective view showing a medical instrument 1 according to an exemplary embodiment of the present invention, FIG. 2 is a side view showing a main body and desk of the medical instrument of FIG. 1, FIG. 3 is a perspective view showing the desk of the medical instrument of FIG. 1, FIG. 4 is a cross-sectional view showing a rear detachable member of FIG. 1, and FIG. 5 is a perspective view showing an operation state of the rear detachable member of FIG. 1.

Referring to FIGS. 1 to 3, the medical instrument 1 according to the present exemplary embodiment may include a main body 10 practically conducting medical treatments, a cart 20 including a desk 22 on which the main body 10 is positioned, a front detachable member 30 disposed on the desk 22 and adapted to attach and detach a front portion of the main body 10 to/from the desk 22, and a rear detachable member 40 disposed on the desk 22 and adapted to attach and detach a rear portion of the main body 10 to/from the desk 22. The main body 10 may include at least one of an operation part 12 and a display part 14. The operation part 12 is a part where signals for adjusting various settings, operations, and the like of the main body 10 are inputted. The display part 14 is a part where contents inputted in the operation part 12, an operation state and diagnosis results of the main body 10 are displayed. Hereinafter, the main body 10 including both of the operation part 12 and the display part 14 will be described.

Referring to FIGS. 1 to 3, the front detachable member 30 may include at least one first front fixing part 32 upwardly protruded from a front portion of the desk 22 and adapted to support both side surfaces and front surface of the main body 10, and a second front fixing part 34 movably disposed on the desk 22 and adapted to enable a side of the second front fixing part to close contact with an upper surface of the main body 10.

The at least one first front fixing part 32 may include a protruded rib respectively formed on left and right sides of the desk 22. Specifically, the first front fixing part 32 may include a left rib 32a closely contacting with a front surface and left side surface of the main body 10 and a right rib 32b closely contacting with the first surface and right side surface of the main body 10. The second front fixing part 34 may include a location control part 36 coupled with a guide 24 formed on a front portion of the desk 22 and moved back and forth along the guide 24, and a latching part 38 backwardly protruded from the location control part 36 and closely contacting with an upper surface of the main body 10. The location control part 36 is arranged on an upper surface of the guide 24 and arranged to be movable back and forth. The location control part 36 may be fixed by a coupling member of the guide 24. The guide 24 may include a slot formed thereon in a back and forth direction and adapted to be coupled with the coupling member. The coupling member may include a bolt coupled with the slot of the guide 24 and the location control part 36. The latching part 38 is protruded from a rear portion of the location control part 36 to a front portion of the main body 10. An end portion of the latching part 38 may be formed into a '¬'-shape to be conformed to shapes of the upper and front surface of the main body 10, so that the end portion of the latching part 38 is in close contact with the upper and front surface of the main body 10 at the same time.

Referring to FIGS. 3 to 5, the rear detachable member 40 may include a first rear fixing part 42 disposed on another region of the desk different from a region where the main body 10 is seated, a second rear fixing part 44 disposed on an upper portion of the at least one first rear fixing part 42 in such a manner as to be elevated and rotated, and may include a latching protrusion 44b latched on an upper surface of the main body 10, and a third rear fixing part 46 connected at a side with the first rear fixing part 42 and connected at the other side with the second rear fixing part 44 and adapted to elastically support the second rear fixing part 44. The rear detachable member 40 may be respectively disposed on left and right sides of the rear portion of the desk 22, so that left and right sides of the rear portion of the main body 10 are fixed. However, a plurality of rear detachable members 40 may be formed on the left and right sides of the rear portion of the desk 22, and at least one rear detachable member 40 may be disposed on both sides or rear side of the main body 10.

The first rear fixing part 42 may include a first boss 42a upwardly protruded from the desk 22 and formed into a cylindrical shape. In this instance, a through hole 42b passing through upper and lower sides of the desk 22 is formed inside the first rear fixing part 42.

The second rear fixing part 44 may include a second boss 44a downwardly protruded from a lower portion of the second rear fixing part 44, and may be formed into a cylindrical shape, so that the second boss 44a is rotatably inserted into the first boss 42a. The first and second bosses 42a and 44a may be coupled to be slidingly moved with respect to each other. Specifically, the second boss 44a may be inserted in an inner side or outer side of the first boss 42a. Hereinafter, the second boss 44a is inserted in the outer side of the first boss 42a. The latching protrusion 44b may be horizontally protruded from the upper portion of the second rear fixing part 44 so as to be latched to the upper surface of the main body 10 seated on the desk 22.

The third rear fixing part 46 may include a rod 47 connected at its top with the second rear fixing part 44 and passing through the through hole 42b, and an elastic member 48 disposed between a lower portion of the rod 47 and a lower portion of the first rear fixing part 42. The rod 47 may have a diameter less than that of the through hole 42b. A lower portion of the rod 47 may be disposed in the lower portion of the desk 22. The lower portion of the rod 47 may have a latching rim 47a on which a lower portion of the elastic member 48 is latched. The elastic member 48 may include a spring connected at an end of the spring with the latching rim 47a and connected at the other end of the spring with the lower end of the first rear fixing part 42. As another example of the third rear fixing part 46, the third rear fixing part 46 may include an elastic member passing through the through hole 42b of the first boss 42a and connected at an upper end of the elastic member with the second rear fixing part 44, and a latching rim disposed on a lower end of the elastic member and latched to a lower portion of the first rear fixing part 42. However, detailed descriptions of the other example of the third rear fixing part including the elastic member and the latching rim will be herein omitted.

As for the medical instrument 1 configured as described above, a process in which the main body 10 is mounted to and separated from the desk will be herein described.

The main body 10 is seated on the desk 22 of the cart 20 in such a manner as to be positioned between the first front fixing part 32 and the first rear fixing part 42, the front portion of the main body 10 is fixed to the desk 22 using the second front fixing part 34, and the rear portion of the main body 10 is fixed to the desk 22 using the second rear fixing part 44. Accordingly, the main body 10 and the cart 20 may be simultaneously used, so that the medical instrument is more easily used in hospital and the like. Hereinafter, a process in which the main body 10 is mounted to the desk 22 will be described in detail.

The main body may be positioned between the first front fixing part 32 and the first rear fixing part 42, so that the first front fixing part 32 supports front surface and both side surfaces of the main body 10, and the first rear fixing part 42 supports both side surfaces of the main body 10. Specifically, the left rib 32a of the first front fixing part 32 may support the front surface of the main body 10 and a left side surface of the front portion of the main body 10, thereby preventing the main body 10 from being moved to the left and front, and the right rib 32b of the first front fixing part 32 may support the front surface of the main body 10 and a right side surface of the front portion of the main body 10, thereby preventing the main body 10 from being moved to the right and front. Also, the first rear fixing part 42 may support left and right side surfaces of the rear portion of the main body 10, thereby preventing the main body 10 from being moved to the right and left.

Next, the location control part 36 of the second front fixing part 34 may be moved backwardly along the guide 24 of the desk 22, so that the latching part 38 of the second front fixing part 34 is in close contact with the front portion of the main body 10. When the latching part 38 is in close contact with the front portion of the main body 10, the location control part 36 is coupled with and fixed on the guide 24. Since the latching part 38 is in close contact with the upper surface of the main body 10, the front portion of the main body 10 is prevented from being upwardly separated from the first front fixing part 32.

Referring to FIG. 5, when the second front fixing part 34 is completely fixed as described above, the second rear fixing part 44 is upwardly lifted from the first rear fixing part 42. When the latching protrusion 44b of the second rear fixing part 44 is located above the upper surface of the main body 10, the second rear fixing part 44 is rotated by a certain angle with respect to the first rear fixing part 42, so that the latching protrusion 44b is disposed above the upper surface of the main body 10. Next, when a force exerting on the second rear fixing part 44 is removed, the latching protrusion 44b is brought into close contact with the upper surface of the main body 10 by an elastic force of the third rear fixing part 46. Accordingly, the rear detachable member 40 may prevent the main body 10 from being upwardly separated from the desk 22, and elastically support the rear portion of the main body 10 seated on the desk 22. The rear detachable member 40 may absorb any impact or vibration transmitted to the main body 10 when elastically and upwardly supporting the main body 10, thereby preventing damage to the main body 10.

In addition, a process in which the main body 10 is separated from the desk 10 will be performed in reverse order of the process in which the main body 10 is mounted to the desk 22. Specifically, the second rear fixing part 44 may be rotated to thereby separate the latching protrusion 44b from the upper surface of the main body 10. When the latching protrusion 44b is separated from the upper surface of the main body 10, the second rear fixing part 44 is downwardly moved along the first rear fixing part 42 by the elastic force of the third rear fixing part 46. Next, the location control part 36 is moved to the front to separate the latching part 38 from the front portion of the main body 10. When the second rear fixing part 44 and the second front fixing part 34 are separated from the main body 10, the main body 10 positioned between the first front fixing part 32 and the first rear fixing part 42 is upwardly lifted and separated from the desk 22. As a result, the main body 10 may be movable to various locations, and data stored in the main body 10 may be directly used.

Figure 6:
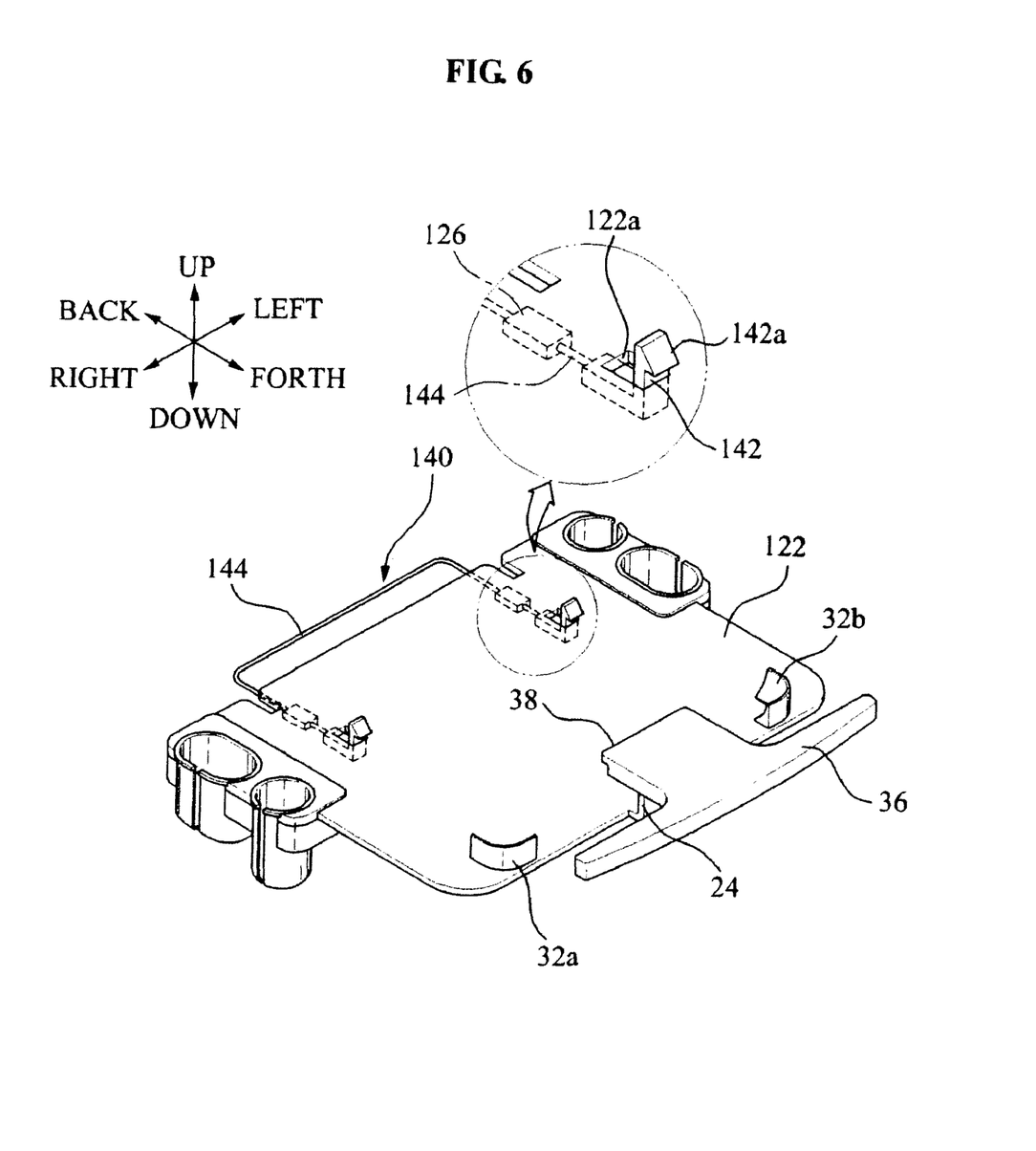
FIG. 6 is a perspective view showing a desk of a medical instrument according to another exemplary embodiment of the present invention.
Figure 7:
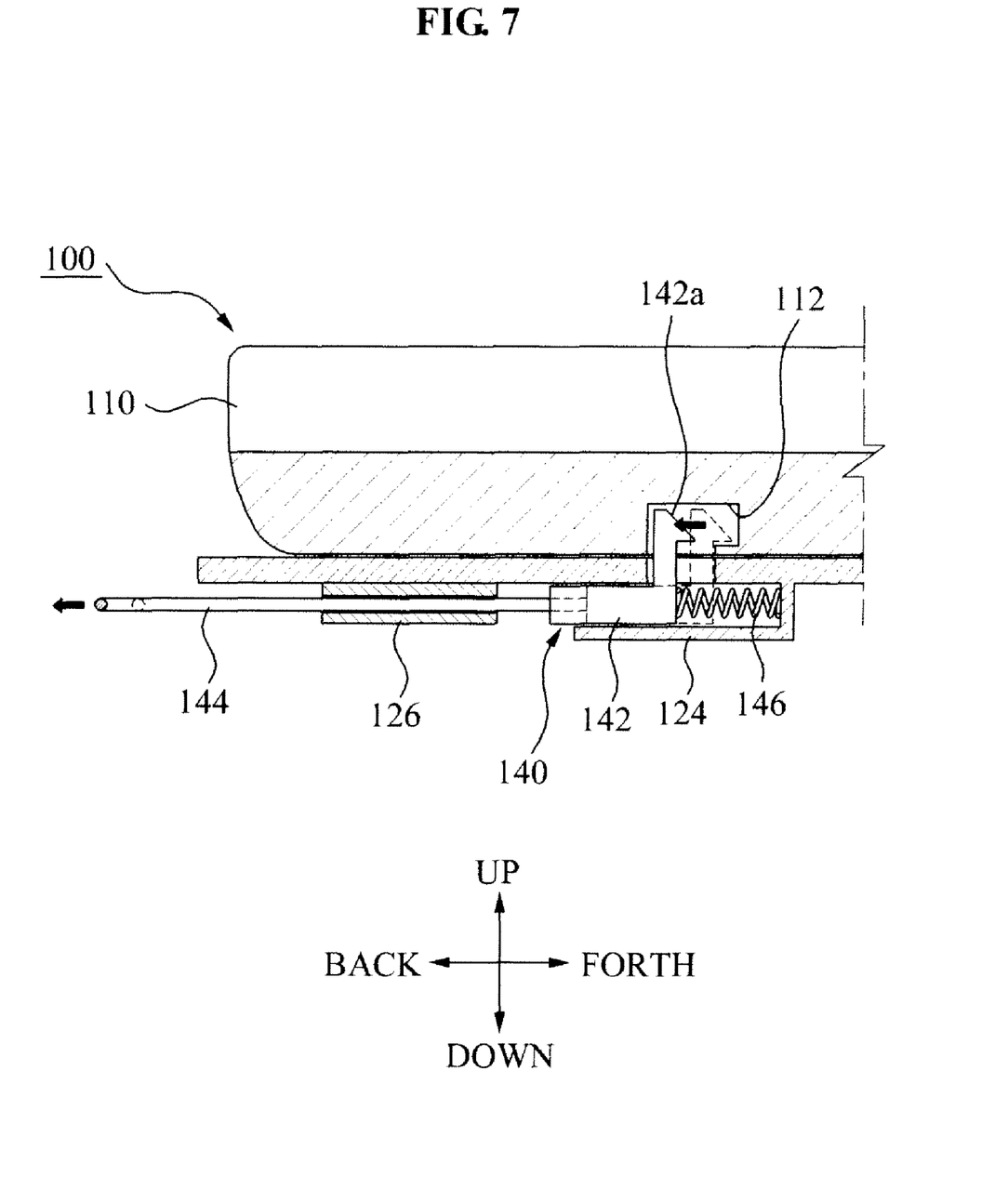
FIG. 7 is a cross-sectional view showing an operation state of a rear detachable member of FIG. 5.

FIG. 6 is a perspective view showing a desk of a medical instrument 100 according to another exemplary embodiment of the present invention, and FIG. 7 is a cross-sectional view showing an operation state of a rear detachable member of FIG. 5.

Identical reference numerals shown in FIGS. 6 and 7 and FIGS. 1 to 5 may denote identical components. Hereinafter, only components of the medical instrument 100 of FIGS. 4 and 5 which are different from those of the medical instrument 1 of FIGS. 1 to 5 will be described in detail. A main body 110 according to the present exemplary embodiment may include a latching groove 112 formed on a lower portion thereof, and a rear detachable member 140 is detachably coupled to the latching groove 112 when the main body 110 is seated on a desk 122. Specifically, the rear detachable member 140 may include a first rear fixing part 142 disposed on a region where the main body 110 is seated on the desk 122 and inserted in and coupled with the latching groove 112 when the main body 110 is seated on the desk 122, a second rear fixing part 144 having a side thereof connected with the first rear fixing part 142 and, at the other side of the second rear fixing part 144, exposed outwardly from a rear portion of the desk 122, and a third rear fixing part 146 disposed between any one of the first and second rear fixing parts 142 and 144 with the desk 122 and adapted to elastically support the first rear fixing part 142.

A plurality of latching grooves 112 may be provided on the lower portion of the main body 110. A through hole 122a may be respectively formed on the desk 112 to correspond to the plurality of latching grooves 112. The through hole 122a may be elongatedly formed in a moving direction of the first rear fixing part 142, so that the first rear fixing part 142 is inserted in the latching groove 112 while moving when the main body 110 is seated on the desk 122. According to the present exemplary embodiment, the latching groove 112 is respectively formed on left and right sides of the lower portion of the main body 110, and the first rear fixing part 142 is moved in a back and forth direction when the main body 110 is seated on the desk 122.

The first rear fixing part 142 may vertically pass through the through hole 122a. The first rear fixing part 142 may include a latching protrusion 142a formed on an upper portion thereof, so that the latching protrusion 142a is inserted in and latched on the latching groove 112. The desk 122 may include a guide receiving part 124 respectively formed below the through hole 122a, so that the first rear fixing part 142 is movably received in the guide receiving part 124.

The second rear fixing part 144 may be movably disposed below the desk 122. The second rear fixing part 144 may have a side thereof connected with the first rear fixing part 142 and, at the other side of the second rear fixing part 144, exposed outwardly from a rear portion of the desk 122. Accordingly, the second rear fixing part 144 may be movable in a back and forth direction together with the first rear fixing part 142 when the main body 110 is seated on the desk 122. The desk 122 may include a guide supporting part 126 formed on the lower portion thereof and adapted to movably support the second rear fixing part 144.

The third rear fixing part 146 may include an elastic member 146 disposed between a lower portion of the first rear fixing part 142 and a lower portion of the desk 122. Specifically, the elastic member 146 may be connected at an end thereof with a front surface of the lower portion of the first rear fixing part 142, and connected at the other end thereof with an inner front surface of the guide receiving part 124.

In the medical instrument 100 configured as described above, the rear portion of the main body 110 may be easily fixed to the desk 122 by a relatively simple operation such that the main body 110 is seated on the desk 122. Specifically, the first rear fixing part 142 may be inserted in the latching groove 112 while moving to the back when the main body 110 is seated on the desk 122, and the latching protrusion 142a may be latched on and coupled with the latching groove 112 while the first rear fixing part 142 is moving to the front. Accordingly, the rear portion of the main body 110 may be prevented from being vertically and laterally moved by the coupling between the latching protrusion 142a of the first rear fixing part 142 and the latching groove 112, and the main body 110 may be elastically supported towards the back on the desk 122 by means of an elastic force of the third rear fixing part 146. Also, the coupling between the latching groove 112 and the latching protrusion 142a of the first rear fixing part 142 is released by a relatively simple operation such as pulling backwardly the second rear fixing part 144, so that the main body 110 is easily separated from the desk 122. In a case of the medical instrument 100 according to the present exemplary embodiment as compared with the medical instrument 1 shown in FIGS. 1 to 5, the operations in which the rear portion of the main body 110 is mounted to and separated from the desk 122 are significantly simple, and the configuration is not exposed to the outside to thereby improve an aesthetic appearance of the medical instrument 100.

Figure 8:
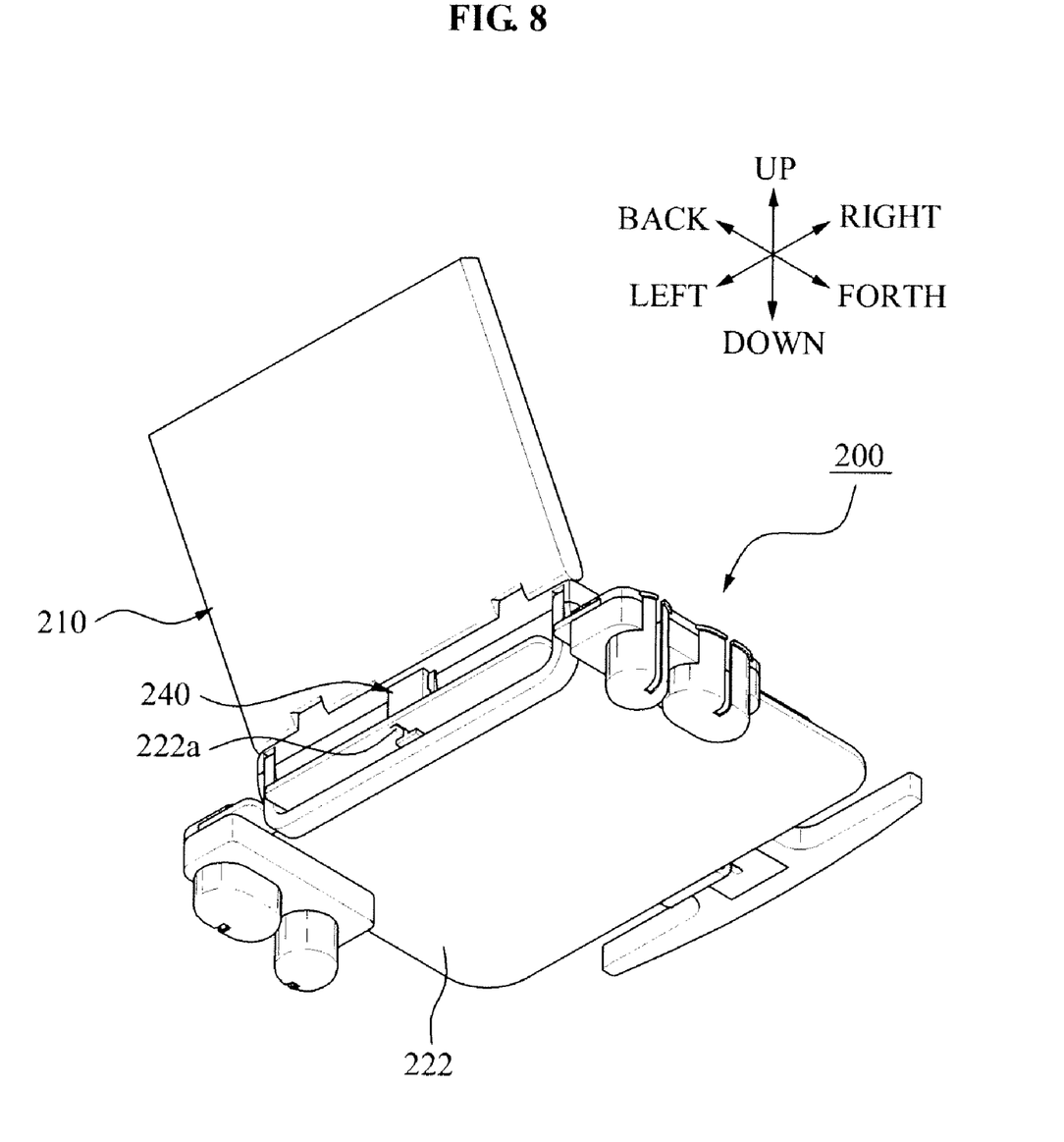
FIG. 8 is a perspective view showing a medical instrument according to still another exemplary embodiment of the present invention.
Figure 9:
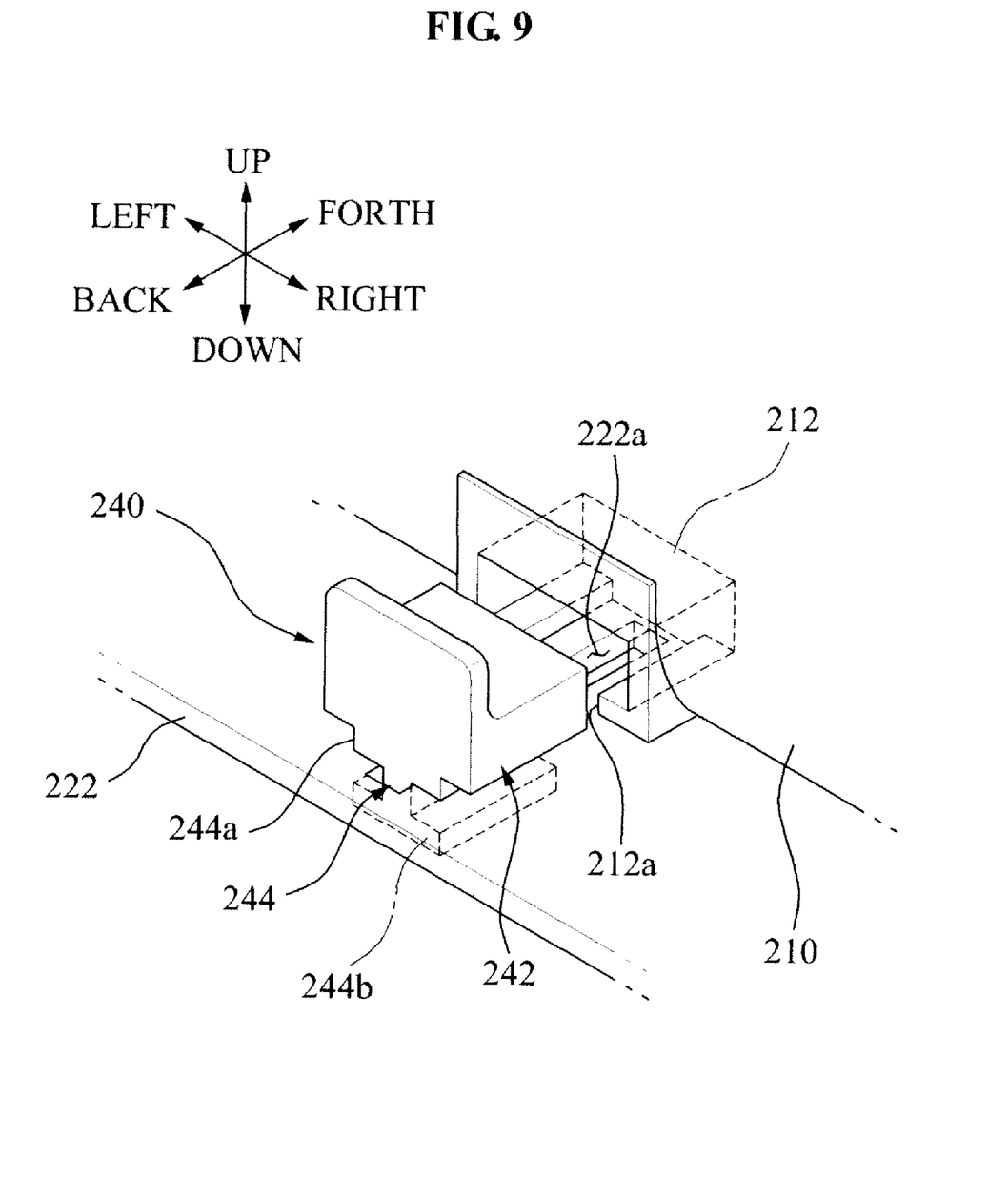
FIG. 9 is a perspective view showing main parts of a main body and desk of the medical instrument of FIG. 8.
Figure 10:
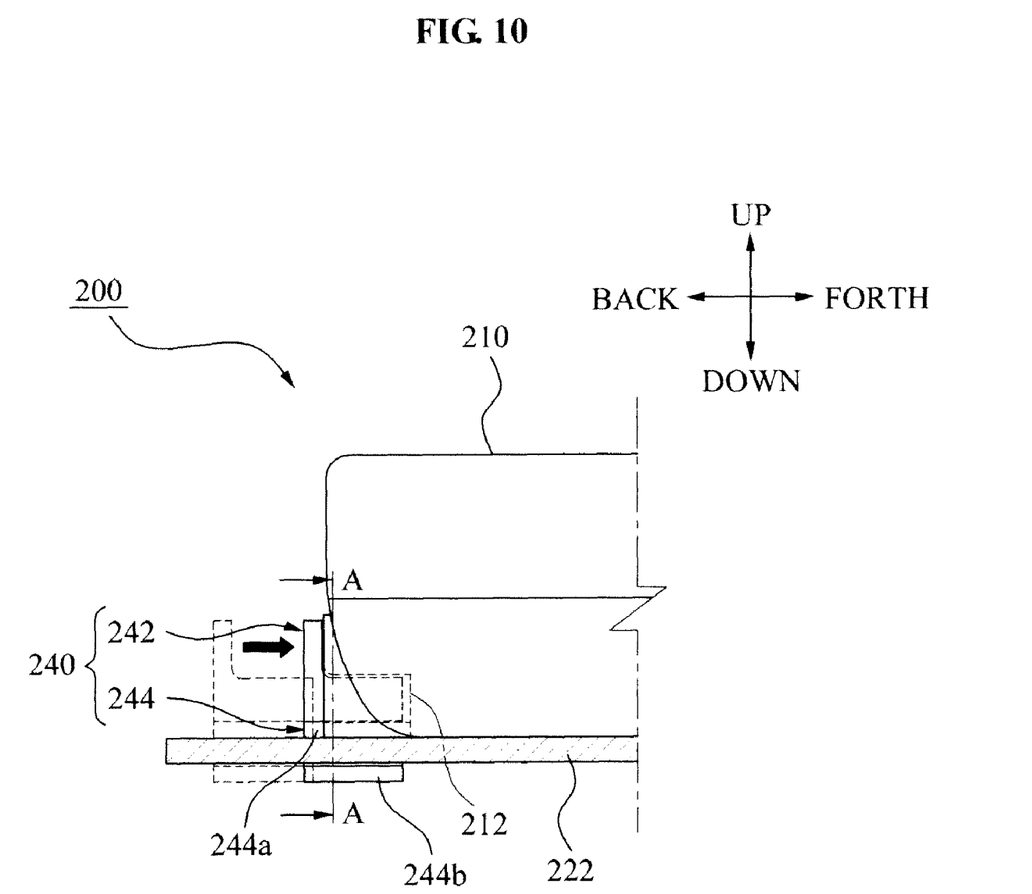
FIG. 10 is a side view showing an operation state of the rear detachable member of FIG. 8.
Figure 11:
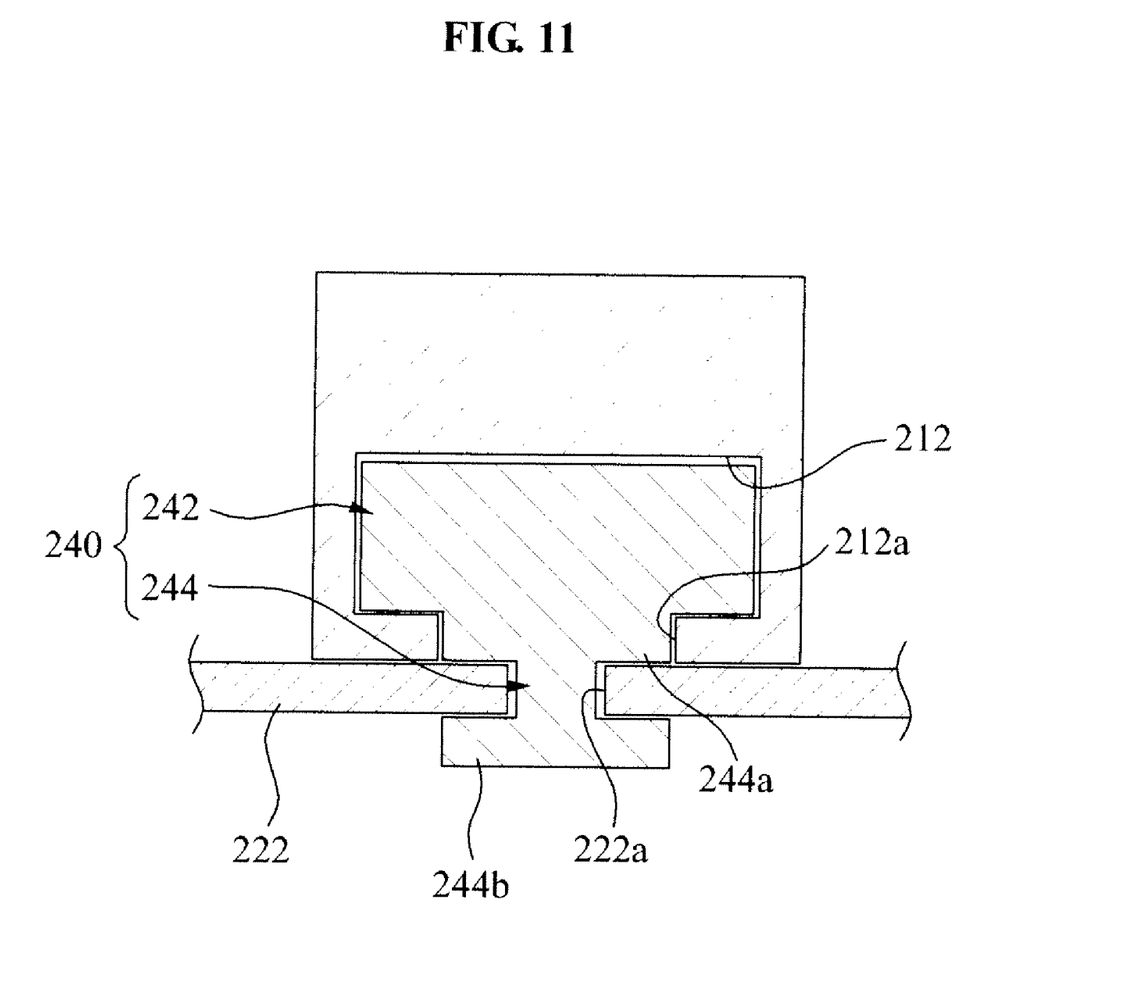
FIG. 11 is a cross-sectional view taken from A-A line of FIG. 10.

FIG. 7 is a cross-sectional view showing an operation state of a rear detachable member of FIG. 5, FIG. 8 is a perspective view showing a medical instrument 200 according to still another exemplary embodiment of the present invention, FIG. 9 is a perspective view showing main parts of a main body 210 and desk of the medical instrument 200 of FIG. 8, and FIG. 10 is a side view showing an operation state of the rear detachable member of FIG. 8.

Identical reference numerals shown in FIGS. 8 and 10 and FIGS. 1 to 5 may denote identical components. Hereinafter, only components of the medical instrument 200 of FIGS. 8 and 10 which are different from those of the medical instrument 1 of FIGS. 1 to 5 will be described in detail. In the medical instrument 200 according to the exemplary embodiment, the main body 210 may include at least one of an operation part 14 and a display part 14, and an insertion groove 212 formed on a rear portion of the main body 210. A desk according to the present exemplary embodiment may include a rear detachable member 240 slidingly disposed on a rear portion of the desk 222 to enable the rear portion of the main body 210 to be attached to and detached from the desk 222, and inserted in or separated from the insertion groove 212.

The insertion groove 212 may be formed on the rear portion of the main body 210. A slot groove 212a may be elongatedly formed on a lower portion of the insertion groove 212 in a back and forth direction. The rear detachable member 240 may include an insertion part 242 inserted in the insertion groove 212, and a moving part 244 disposed on a lower portion of the insertion part 242 and slidingly disposed on the rear portion of the desk 222 in a back and forth direction. The insertion part 242 may be shaped to conform to the insertion groove 212, elongatedly formed in a back and for the direction, and disposed on the rear portion of the desk 222 to face the insertion groove 212. A middle portion of the moving part 244 may pass through a slot 222a formed on the rear portion of the desk 222, so that the moving part 244 is slidingly moved in a back and forth direction along the slot 222a. The moving part 244 may include upper and lower rails 244a and 244b respectively formed on upper and lower portions of the moving part 244, and the upper and lower rails 244a and 244b may have a width greater than that of the slot 222a. Accordingly, the moving part 244 of a lower portion of the insertion part 242 may be formed into 'I' shape in its cross-sectional area. The upper rail 244a may be formed to have a width less than that of the slot groove 212a, so that the upper rail 244a is inserted in the slot groove 212a when the insertion part 242 is inserted in the insertion groove 212. Specifically, the slot 222a may formed on the rear portion of the desk 222 to have a width less than the slot groove 212a to correspond to the slot groove 212a.

In the medical instrument 200 configured as described above, the rear portion of the main body 210 may be easily fixed to the desk 222 by a relatively simple operation such that the main body 210 is seated on the desk 222, and then the rear detachable member 240 is slidingly moved to the forth. Specifically, the main body may be prevented from being vertically and laterally moved when the insertion part 242 of the rear detachable member 240 is inserted in the insertion groove 212 of the main body 210. Referring to FIG. 10, the rear portion of the main body 210 may be easily separated from the desk 222 by a relatively simple operation such as moving backwardly the rear detachable member 240. In a case of the medical instrument 200 according to the present exemplary embodiment as compared with the medical instrument 1 shown in FIGS. 1 to 5, the operations in which the rear portion of the main body 110 is mounted to and separated from the desk 122 are significantly simple, and the configuration is significantly simple. In addition, the main body 210 may be elastically supported towards the back when an elastic member is disposed between the moving part 244 and the desk 222 although not described in the present exemplary embodiment.

As described above, according to the present invention, a main body may be easily mounted to and separated from a desk of a cart by a front detachable member and a rear detachable member, thereby improving utilization and convenience of use of a medical instrument, and also enabling simple maintenance and repair of the main body.

According to the present invention, the rear detachable member may elastically support the main body of the medical instrument to thereby absorb impact transmitted to the main body, thereby preventing damage of the main body.

According to the present invention, the main body separated from the medical instrument may be moved to a desired location to utilize data stored in the main body, thereby improving utilization of the data.

According to the present invention, the main body separated from the medical instrument may be moved to various locations other than hospitals to be used for diagnosis of patients, thereby more easily conducting an ambulatory care.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A medical instrument, comprising:
   a main body including at least one of an operation part and a display part;
   a cart including a desk on which the main body is positioned;
   a front detachable member disposed on the desk and adapted to attach and detach a front portion of the main body to/from the desk; and
   at least one rear detachable member disposed on the desk and adapted to attach and detach a rear portion of the main body to/from the desk and elastically support the rear portion of the main body,
   wherein the at least one rear detachable member includes:
   a first rear fixing part disposed on another region of the desk different from a region where the main body is seated;
   a second rear fixing part disposed on an upper portion of the first rear fixing part in such a manner as to be elevated and rotated, and include a latching protrusion latched on an upper surface of the main body; and
   a third rear fixing part connected at a side with the first rear fixing part and connected at the other side with the second rear fixing part and adapted to elastically support the second rear fixing part,
   wherein the first rear fixing part includes a first boss upwardly protruded and formed into a cylindrical shape, and the second rear fixing part downwardly protruded, formed into a cylindrical shape, and inserted in the first boss in such a manner as to be rotated and elevated.

2. The medical instrument of claim 1 wherein a through hole passing through upper and lower sides of the desk is formed inside the first rear fixing part, and the third rear fixing part includes a rod connected at its top with the second rear fixing part and passing through the through hole, and an elastic member disposed between a lower portion of the rod and a lower portion of the first rear fixing part.

3. The medical instrument of claim 1, wherein the front detachable member includes:
   at least one first front fixing part upwardly protruded from a front portion of the desk and adapted to support both side surfaces and front surface of the main body; and
   a second front fixing part movably disposed on the desk and adapted to enable a side of the second front fixing part to closely contact with an upper surface of the main body.

4. The medical instrument of claim 3, wherein the side of the second front fixing part is shaped to conform to the upper surface and front surface of the main body, so that the side of the second front fixing part is closely contacted with the upper surface and front surface of the main body at the same time.

* * * * *